United States Patent [19]

Stadler et al.

[11] E Re. 31,512

[45] Reissued Jan. 31, 1984

[54] PSEUDOTRISSACCHARIDES, A PROCESS FOR THEIR PRODUCTION AND THEIR USE AS MEDICAMENTS

[75] Inventors: Peter Stadler, Haan; Karl G. Metzger, Wuppertal; Eckart Voss, Cologne; Uwe Petersen, Leverkusen; Hans-Joachim Zeiler, Velbert; Hans-Joachim Kabbe, Leverkusen, all of Fed. Rep. of Germany

[73] Assignee: Bayer Aktiengesellschaft, Leverkusen, Fed. Rep. of Germany

[21] Appl. No.: 260,853

[22] Filed: May 6, 1981

Related U.S. Patent Documents

Reissue of:

[64] Patent No.: 4,235,888
Issued: Nov. 25, 1980
Appl. No.: 52,871
Filed: Jun. 28, 1979

[30] Foreign Application Priority Data

Jul. 22, 1978 [DE] Fed. Rep. of Germany ..... 2832268

[51] Int. Cl.[3] ..... A61K 31/71; C07H 15/22

[52] U.S. Cl. ..... 424/180; 536/13.9

[58] Field of Search ..... 424/180; 536/17, 10, 536/13.7, 13.9, 13.4, 13.6

[56] References Cited

U.S. PATENT DOCUMENTS

| | | | |
|---|---|---|---|
| 3,997,524 | 12/1976 | Nagabhushan | 536/17 |
| 4,048,431 | 9/1977 | Hlavka et al. | 536/17 |
| 4,062,947 | 12/1977 | Wright | 536/17 |
| 4,085,208 | 4/1978 | Mallams et al. | 536/17 |

FOREIGN PATENT DOCUMENTS

| | | |
|---|---|---|
| 2355029 | 1/1978 | France . |
| 1530202 | 10/1978 | United Kingdom . |

*Primary Examiner*—Blondel Hazel
*Attorney, Agent, or Firm*—Sprung, Horn, Kramer & Woods

[57] ABSTRACT

Pseudotrisaccharides of the sisomycin type are provided which are effective an antibacterial agents, particularly against gram-negative microorganisms. The invention also includes methods for the manufacture of the pseudotrisaccharides, compositions containing said pseudotrisaccharides and methods for the treatment of warm-blooded animals using said compounds and compositions.

9 Claims, No Drawings

PSEUDOTRISSACCHARIDES, A PROCESS FOR THEIR PRODUCTION AND THEIR USE AS MEDICAMENTS

Matter enclosed in heavy brackets [ ] appears in the original patent but forms no part of this reissue specification; matter printed in italics indicates the additions made by reissue.

The present invention relates to new pseudotrisaccharides, to processes for their production and to their use as medicaments. In particular, the invention relates to new antibacterially active aminoglycoside antibiotics of the sisomicin type.

Aminoglycoside antibiotics are important substances for effectively combating bacterial infections. However, the appearance of resistant germs in many cases reduces their broad applicability; moreover, side effects such as ototoxicity and nephrotoxicity can occur. In some cases these disadvantages have been successfully removed by forming derivatives. Compounds have now been found which may overcome disadvantages mentioned to a particularly great extent.

According to the invention there are provided pseudotrisaccharides which are compounds of the general formula

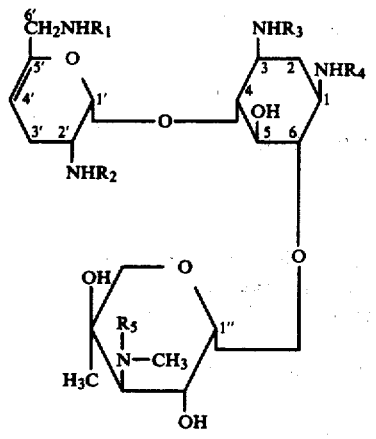

(I)

or salts thereof, in which $R_1$, $R_2$, $R_3$, $R_4$ and $R_5$ independently of one another denote a hydrogen atom or a radical of the general formula $$CH_2-(CH_2)_{n1}-\underset{\underset{OR_6}{|}}{(CH)_{n2}}-A_{n3}-\underset{\underset{OR_6}{|}}{(CH)_{n4}}-CH_2R_7 \qquad \text{(Ia)}$$

in which

A denotes $$-CH{=}CH- \text{ or } [-CH_{(2-n5)}-(CH_2OR_6)_{n5}-]$$

$R_6$ denotes a hydrogen atom or a triarylmethyl, alkyl or acyl radical, or

2 $R_6$ radicals denote an alkylidene radical, $R_7$ denotes a hydrogen atom or $OR_6$, $n_1$ is 0, 1, 2 or 3, $n_2$ is 0, 1, 2, 3, 4 or 5 and $n_3$, $n_4$ and $n_5$ are independently of one another, 0, 1 or 2, the sum of $n_1$, $n_2$, $n_3$ and $n_4$ being from 1 to 5 and the total number of the $OR_6$ groups in at least one of the radicals $R_1$, $R_2$, $R_3$, $R_4$ and $R_5$ being 2 to 6, and at least one of the radicals $R_1$, $R_2$, $R_3$, $R_4$ and $R_5$ being other than a hydrogen atom. Aliyl $R_6$ is, in particular, $C_1$ to $C_4$ alkyl and acyl $R_6$ is, in particular, $C_2$ to $C_4$ alkylcarbonyl, formyl or benzoyl.

Alkylidene formed from 2 radicals $R_6$ is, in particular, $C_1$ to $C_6$ alkylidene.

Triarylmethyl is, in particular, triphenylmethyl. Triarylmethyl can also be, for example, tri-(o-, m- or p-$C_1$-$C_4$-alkyl-phenyl)-methyl, tri-(o-, m-, p-chlorophenyl)-methyl, etc.

Preferred compounds within the formula (I) are those in which $R_4$ and one of the radicals $R_1$ and $R_2$ are other than hydrogen and the radicals $R_3$ and $R_5$ and the other one of the radicals $R_1$ and $R_2$ denote hydrogen. Very particularly preferred compounds are those in which $R_1$, $R_2$, $R_3$ and $R_5$ denote hydrogen and $R_4$ is other than hydrogen.

Within these compounds, and other compounds of formula (I), those compounds in which $n_3$ and $n_4$ denote 0 and the sum of $n_1$ and $n_2$ is 1, 2 or 3 are of particular interest.

The compounds according to the invention and their pharmaceutically usable salts exhibit powerful antibacterial properties against a number of germs and an exceptionally good tolerance.

The pharmaceutically usable salts are especially acid-addition salts and are derived, in particular, from inorganic or organic acids, such as sulphuric acid, phosphoric acid, nitric acid, hydrochloric acid, hydrobromic acid, acetic acid, pripionic acid, ascorbic acid and pamoic acid and citric acid.

Examples of suitable radicals $R_1$ to $R_5$ are straight-chain polyhydroxyalkyl radicals, such as 2,3-dihydroxypropyl, 2,3,4-trihydroxybutyl, 2,3,4,5-tetrahydroxypentyl, 2,3,4,5,6-pentahydroxyhexyl, 3,4-dihydroxybutyl, 3,4,5-trihydroxypentyl, 3,4,5,6-tetrahydroxyhexyl, 4,5-dihydroxypentyl, 4,5,6-trihydroxyhexyl, 4,5-dihydroxyhexyl, 2,3,4-trihydroxypentyl, 2,3,4,5-tetrahydroxyhexyl, 3,4,5,6,7-pentahydroxyheptyl, 3,4,5,6-tetrahydroxyheptyl, 2,4,5-trihydroxypentyl, 2,4,5,6tetrahydroxyhexyl, 2,4,5-trihydroxyhexyl, 2,5-dihydroxypentyl and 2,3-dihydroxypentyl, branched polyhydroxyalkyl radicals, such as 2,4-dihydroxy-3-hydroxymethylpentyl and 2,2-bis-hydroxymethylpropyl, straight-chain polyhydroxyalkenyl radicals, such as 4,5-dihydroxy-pent-2-en-1-yl, 4,5,6-trihydroxy-hex-en-1-yl and 4,5-dihydroxy-hex-2-en-1-yl, and polyhydroxyalkyl groups which are acylated and alkylated on the OH groups, such as 2,3,4,5-tetraacetoxypentyl, 2,3,4,5-tetrabenzoyloxyhexyl, 2,3,-dimethoxypropyl, 2,3,4-trihydroxy-5-methoxypentyl and 2,3-O-isopropylidenepropyl.

The radicals listed above are only to be understood as examples. They all contain at least one—in most cases several—chiral C atoms and exist as optically pure diastereomers or diastereomer mixtures. It can be advantageous to use the compounds according to the invention in the form of optically pure products.

Racemate mixtures can be separated into the pure racemates in a known manner on the basis of the physicochemical differences of the constituents, for example by chromatography and/or fractional crystallisation.

Pure racemates can be resolved according to known methods, for example by recrystallisation from an optically active solvent, with the aid of micro-organisms or by reaction with an optically active acid or base which forms salts with the racemic compound and separation of the salts obtained in this manner, for example on the basis of their different solubilities, into the diastereomers from which the antipodes can be liberated by the action of suitable agents. Particularly customary optically active acids are, for example, the d- and l-forms of tartaric acid, di-o-toluyltartaric acid, malic acid, mandelic acid, camphorsulphonic acid or quinic acid. Suitable optically active bases are, for example, optically active α-phenylethylamine, α-(1-naphthyl)-ethylamine, quinine, cinchonidine and brucine. Advantageously, the more active of the two antipodes is isolated.

According to the invention it is however also possible to obtain the end products in the form of the pure racemates or optical antipodes by employing starting substances, containing one or more asymmetrical C atoms, in the form of the pure race-mates or optical antipodes.

Specific examples which may be mentioned of the active compounds according to the invention are: 1-N-[S-2,3-dihydroxypropyl]-sisomicin, 1-N-[R-2,3-dihydroxypropyl]-sisomicin, 1-N-[S,R-2,3,4-trihydroxybutyl]-sisomicin, 1-N-[R,S-2,3,4-trihydroxybutyl]-sisomicin, 1-N-[R,R-2,3,4-trihydroxybutyl]-sisomicin, 1-N-[S,S-2,3,4-trihydroxybutyl]-sisomicin, 1-N-[S,S,R-, 1-N-[R,R,S-, 1-N-[R,S,R-, 1-N-[S,R,S-, 1-N-[S,R,R-, 1-N-[R,S,S-, 1-N-[R,R,R- and 1-N-[S,S,S-2,3,4,5-tetrahydroxypentyl]-sisomicin, 1-N-[S,R,S,R,R-, 1-N-[R,R,S,S-, 1-N-[R,S,R,R-, 1-N-[S,R,R,R,-, 1-N-[R,S,S,S-, 1-N-[R,R,R,R-, 1-N-[S,S,S,S-, 1-N-[S,S,S,R-, 1-N-[R,S,S,R-, 1-N-[S,R,R,S-, 1-N-[S,R,S,R-, 1-N-[R,R,S,R-, and 1-N-[S,S,R,S-2,3,4,5,6-pentahydroxyhexyl]-sisomicin, 1-N-[S,S,R-, 1-N-[R,R,S-, 1-N-[R,S,R-, 1-N-[S,R,S-, 1-N-[S,R,R-, 1-N-[R,S,S-, 1-N-[R,R,R- and 1-N-[S,S,S-3,4,5,6-tetrahydroxyhexyl]-sisomicin, 1-N-[R,S,R- 2,4,5,6-tetrahydroxyhexyl]-sisomicin, 1-N-[S,R,R-, 1-N-[R,S,S-, 1-N-[R,R,R-, 1-N-[S,S(S-, 1-N-[S,S,R-, 1-N-[R,R,S-, 1-N-[R,S,R- and 1-N-[S,R,S-3,4,5-trihydroxyhexyl]-sisomicin, 1-N-[S,R- and 1-N-[R,S-4,5-dihydroxyhexyl]-sisomicin, 1-N-[S,R-, 1-N-[R,S-, 1-N-[R,R- and 1-N-[S,S-3,4,5-trihydroxypentyl]-sisomicin, 1-N-[S,R-, 1-N-[R,S-, 1-N-[R,R- and 1-N-[S,S-3,4-dihydroxypentyl]-sisomicin, 1-N-[S- and 1-N-[R-2,5-dihydroxypentyl]-sisomicin, 1-N-[R,S-, 1-N-[S,R-, 1-N-[S,S- and 1-N-[R,R-2,4,5-trihydroxypentyl]-sisomicin, 1-N-[R,R- and 1-N-[S,S-2,4-dihydroxypentyl]-sisomicin, 1-N-[R- and 1-N-[S-2,4-dihydroxybutyl]-sisomicin, 1-N-[2,2-bis-hydroxypropyl)-sisomicin, 1-N-[S,R,S-2,3,4-trihydroxy-3-C-hydroxymethylpentyl]-sisomicin, 1-N-[S,R-, 1-N-[R,S-, 1-N-[R,R- and 1-N-[S,S-4,5,6-trihydroxy-hex-2,3-enyl]-sisomicin, 1-N-[S,R- and 1-N-[R,S-4,5-dihydroxyhex-2,3-enyl]-sisomicin, 1-N-[S- and 1-N-[R-4,5-dihydroxypent-2,3-enyl]-sisomicin, 1-N-(2-hydroxy-3-methoxypropyl)-sisomicin, 1-N-(2,3-dimethoxypropyl)-sisomicin, 1-N-(3-hydroxy-2-methoxypropyl)-sisomicin, 1-N-[S,S,R-2,3,4-trihydroxy-5-methoxypentyl]-sisomicin, 1-N-[S,R,R,R,-2,4,5,6-tetrahydroxy-3-methoxyhexyl]sisomicin, 1-N-[S,R,R,S-2,3,4,5-tetrahydroxy-6-methoxyhexyl]-sisomicin, 1-N-(2,3-diacetoxypropyl)-sisomicin, 1-N-[S,R,S-2,3,4,5-tetraacetoxypentyl]-sisomicin, 1-N-(2,3-O-isopropylidenepropyl)-sisomicin, 1-N-(2,3-dihydroxypropyl)-6'-N-hydroxyethylsisomicin, 1-N-[S,S,R-2,3,4,5-tetrahydroxypentyl]-6'-N-hydroxyethyl-sisomicin, 1,6'-di-N-)2,3-dihydroxypropyl)-sisomicin, 1-N-[S,S,R-2,3,4,5-tetrahydroxypentyl]-6'-N-(2,3-dihydroxypropyl)-sisomicin, 1-N-[S,S,R-2,3,4,5-tetrahydroxypentyl]-2'-N-hydroxyethyl-sisomicin, and 1,2'-di-N-(2,3-dihydroxypropyl)-sisomicin.

The invention further relates to a process for the production of a compound of the present invention in which (a) a selectively acylated or sulphenylated compound of the formula (II)

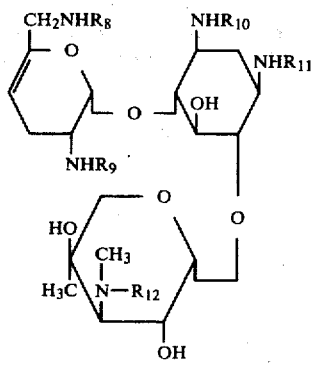

(II)

in which $R_8$, $R_9$, $R_{10}$, $R_{11}$ and $R_{12}$ denote a hydrogen atom or —SR' or —CO—A', with the proviso that at least one of the radicals $R_8$ to $R_{12}$ denotes a hydrogen atom and at least one of the radicals $R_8$ to $R_{12}$ denotes —SR' or —CO—A', in which R' denotes an optionally substituted phenyl, diphenylmethyl or triphenylmethyl radical and A' denotes $-(CH_2)_{n6}-B$ or $-O-C(-(CH_2)_{n7}-B)(-(CH_2)_{n8}-H)(-(CH_2)_{n9}-H)$ in which B denotes a hydrogen atom or an optionally substituted phenyl radical and $n_6$, $n_7$, $n_8$ and $n_9$ are, independently of one another, 0, 1, 2, 3, 4 or 5, is reacted with an aldehyde of the general formula $$HOC-(CH_2)_{n1}-(CH)_{n2}(OR_6)-A_{n3}-(CH)_{n4}(OR_6)-CH_2R_7 \quad \text{(III)}$$

in which $R_6$, $R_7$, A, $n_1$, $n_2$, $n_3$ and $n_4$ have the above-mentioned meaning, in the presence of a hydrogen donor reducing agent, and the protective groups —S—R' or —CO—A' are then split off, (b) for the production of compounds of formula (I) in which $n_1$ is 0, a compound of formula (II) is reacted with an epoxy compound of the general formula

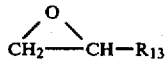

in which $R_{13}$ denotes $(CH)_{(n2\ 1)}(OR_6)-A_{n3}-(CH)_{n4}(OR_6)-CH_2-R_7$ and $R_6$, $R_7$, A, $n_2$, $n_3$ and $n_4$ have the above-mentioned meanings, (c) a compound of formula (II) in which $R_8$, $R_9$, $R_{10}$, $R_{11}$ and $R_{12}$ denote a hydrogen atom, or an acid addition salt thereof is reacted with a compound of formula (III) and a hydrogen donor reducing agent, or (d) a compound of the general formula

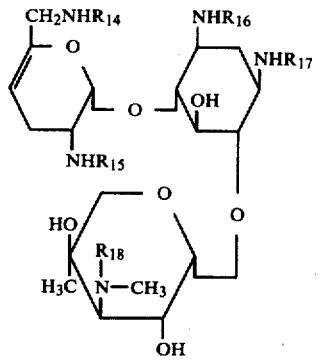

(IV)

in which one or two of the radicals $R_{14}$, $R_{15}$, $R_{16}$, $R_{17}$ and $R_{18}$, preferably one or two of the radicals $R_{14}$, $R_{15}$ and $R_{17}$, denote a radical of the general formula $$-CO-(CH_2)_{n1}-\underset{\underset{OR_6}{|}}{(CH)_{n2}}-A_{n3}-\underset{\underset{OR_6}{|}}{(CH)_{n4}}-CH_2R_7 \quad \text{(Ib)}$$

and the other radicals of $R_{14}$, $R_{15}$, $R_{16}$, $R_{17}$ and $R_{18}$ denote hydrogen atoms, wherein $R_6$, $R_7$, $n_1$, $n_2$, $n_3$, $n_4$ and A have the above-mentioned meanings, is reduced with a hydrogen-containing reducing agent.

Optionally substituted phenyl R is, in particular, phenyl, or phenyl which is substituted by one to three substituents from the series nitro, $C_1$ to $C_4$ alkyl, $C_1$ to $C_4$ alkoxy, $C_1$ to $C_4$ alkoxycarbonyl or phenyl or by 1 to 5 halogen atoms (particularly chlorine or bromine atoms.

Optionally substituted phenyl B is, in particular, phenyl, or phenyl which is substituted by one or two substituents of the group nitro, $C_1$ to $C_4$ alkyl, $C_1$ to $C_4$ alkoxy, phenyl or halogen.

The compounds of the formula (II) are obtained by a process in which sisomicin is reacted, for example, with o-nitrophenylsulphenic acid p-nitrophenyl ester in the presence of a base, in an inert solvent at temperatures between −30° and +50° C., water being added if appropriate. In this process, one to four mols of the sulphenic acid ester are employed per one mol of sisomicin, depending on how many amino groups are to be protected. Further reagents by means of which protective groups can be introduced are tritylsulphenyl chloride, o-nitrophenylsulphenyl chloride, 2,4-dinitrophenylsulphenyl chloride, 2,4,5-trichlorophenylsulphenyl chloride, pentachlorophenylsulphenyl chloride, 2,4-dinitrophenylsulphenic acid p-nitrophenyl ester, 2,4,5-trichlorophenylsulphenic acid p-nitrophenyl ester, pentachlorophenylsulphenic acid p-nitrophenyl ester, acetic anhydride, acetyl chloride, di-t-butyl pyrocarbonate and diethyl pyrocarbonate.

The sulphenyl protective groups can be split off with acids, e.g. 0,1 n hydrochloric acid in methanol, by nucleophiles, such as for example, $H_2S$ or thiophenol or by combinations of both. The other protective groups can be split off with aqueous alkali metal hydroxide or alkaline earth metal hydroxide or with acids, such as trifluoroacetic acid, perchloric acid or boron trifluoride etherate.

The reductive alkylation with an aldehyde of the formula (III) in the presence of a hydrogen donor reducing agent is usually carried out at room temperature in the presence of air, although it can be more favourable to carry out the reaction under an inert gas (argon or nitrogen). The reaction is usually completed very rapidly, frequently in less than 60 minutes, and this can be established by determinations by thin layer chromatography.

Hydrogen donor reducing agents which are used in this process include alkylaminoboranes, for example dimethylaminoborane, diethylaminoborane and morpholinoborane, tetraalkylammonium cyanohydrides (for example tetrabutylammonium cyanoborohydride), alkali metal borohydrides, for example sodium borohydride, and, preferably alkali metal cyanoborohydrides, for example lithium cyanoborohydride and sodium cyanoborohydride.

The process is usually carried out in an inert solvent. The solvent can be an organic or inorganic solvent, in which the selectively protected 4,6-di-O-(aminoglycosyl)-1,3-diaminocyclitol and the other reagents are soluble and which under the reaction conditions as far as possible reduces or prevents side reactions. Although anhydrous aprotic solvents can advantageously be employed, for example tetrahydrofurane if the reducing agent is morpholinoborane, a protic solvent is nevertheless customarily used. A suitable protic solvent is, for example, a lower alkanol or, preferably, water or an aqueous lower alkanol, preferably aqueous methanol or ethanol, or acetone or other solvent systems which contain water, such as aqueous dimethylformamide, aqueous hexamethylphosphoramide, aqueous tetrahydrofurane or aqueous ethylene glycol dimethyl ether.

The process is usually carried out in a pH range from 1 to 11, and preferably at pH 4 to 8.

The aldehydes used in the process are carbohydrates or derivatives thereof. They are in most cases accessible by known syntheses, such as are described, for example, in "Methods in Carbohydrate Chemistry", Academic Press—New York and London—Volumes I–V. They can be employed for the reductive alkylation either in the free form or as acetals—for example as dimethyl acetals of the type $$\begin{matrix} H_3CO \\ H_3CO \end{matrix}\!\!>CH-(CH_2)_{n1}-\underset{\underset{OR_6}{|}}{(CH_2)_{n2}}-A_{n3}-\underset{\underset{OR_6}{|}}{(CH)_{n4}}-CH_2R_7$$

wherein $R_6$, $R_7$, A, $n_1$, $n_2$, $n_3$ and $n_4$ have the meaning already given.

When acetals are used, the reaction is carried out in the presence of mineral acids or organic acids, such as acetic acid, whereupon the acetal is split and the aldehyde liberated reacts immediately with the appropriate amino group of the aminotrisaccharide derivatives of the formula (II).

An important advantage of the use, according to the invention, of carbohydrates or derivatives thereof for the reductive introduction of polyhydroxyalkyl or polyhydroxyalkenyl radicals is the fact that a large number of polyfunctional and, above all, optically pure aldehyde compounds are available in the form of sugars for reductive alkylation reactions. Particular consideration should be given to the fact that the biological properties of the pure components of diastereomer mixtures of the aminoglycoside antibiotics according to the invention usually differ significantly from one another.

The sugars used according to the invention are, for example, D- or L-glyceraldehyde, tetroses, such as D-erythrose, pentoses, such as D-ribose or L-arabinose, or hexoses, such as D-glucose or D-galactose. Also of importance are desoxy derivatives of sugars, such as 2-desoxy-D-ribose, 2-desoxy-D-glucose, 2-desoxy-D-galactose, 6-desoxy-L-mannose, 6-desoxy-D-glucose, 5-desoxy-D-ribose, 2,6-di-desoxy-D-glucose or -L-glucose, 2,3-di-desoxy-D-glucose and 2,3,6-tri-desoxy-L-mannose, and unsaturated sugars, such as pseudoglucal or pseudorhamnal. The above-mentioned compounds are only a selection, which is intended to illustrate the process according to the invention.

If sugars are used which carry alkyl, acyl or alkylidene radicals on one or more OH groups, in addition to the 1-OH group, compounds of the formula I with alkoxy, acyloxy or O-alkylidene radicals in the newly introduced group R are obtained. Examples of such sugar derivatives are 2,3-O-isopropylidene-D-glyceraldehyde, 3-O-methyl-D-glucose, 5-O-methyl-D-ribose or 2,3,4,5-tetra-O-acetyl-L-arabinose. These derivatives are accessible by the known processes of carbohydrate chemistry.

In a preferred embodiment of the process (a) according to the invention, selectively blocked sugar derivatives of the formula (III) in which $R_7$, A, $n_1$, $n_2$, $n_3$ and $n_4$ have the meaning already given and $R_6$ denotes only acyl, that is to say which are present in the aldehyde form and not in the hemi-acetal form, are employed as the aldehyde component for the reductive alkylation of the selectively protected aminotrisaccharides of the formula (II), all the O-protective nd N-protective groups present in the molecule are then split off and the compounds of the formula (I) are thus obtained.

In the process (b), in the case of epoxy compounds which are relatively slow to react, the reaction is appropriately carried out at elevated temperature. The reactions in question otherwise proceed in accordance with the methods which are in themselves known.

After splitting off the protective groups present in the molecule, compounds of the formula I which are substituted by $—CH_2—CHOH—R_{13}$ on one or two of the N atoms present are obtained, and $R_{13}$ has the meaning indicated above.

In the process (c), the appropriate aminotrisaccharides of the formula (II) in which, in this case, $R_8$ to $R_{12}$ represent hydrogen, or acid addition salts thereof in which some of the amino groups present in the molecule have been neutralised by mineral acids, are reacted with one to two equivalents of the polyhydroxyaldehyde (III) in the presence of a hydrogen donor reducing agent, such as sodium cyanoborohydride or dimethylaminoborane, in a suitable solvent. After the reaction, the N-polyhydroxyalkylaminotrisaccharides of the formula I are isolated directly, for which it may be necessary, in some cases, to separate off the required end products from undesired by-products of column chromatography.

The process (d) is usually carried out in an inert organic solvent in which the starting compounds and the reducing agent are soluble and which as far as possible suppresses side reactions. Examples of such solvents are ethers, such as dioxane, tetrahydrofurane, diethylene glycol dimethyl ether and the like. Preferred reducing agents are aluminium hydrides and borohydrides, such as lithium aluminium hydride, aluminium hydride, diborane and the like. In general, diborane is preferably used as the reducing agent. If, however, the starting compound has a double bond, lithium aluminium hydride is preferably used.

The invention furthermore comprises mono-N-acyl and di-N-acyl derivatives of the 4,6-di-O-aminoglycosyl-1,3-diaminocyclitols, of the formula (IV) as defined above.

These compounds are valuable intermediate products for the preparation of the compounds of the formulae (I), but likewise have a broad spectrum of antibacterial activity and a favourable level of tolerance.

The compounds of the formula (IV) are obtained by a process in which sisomicin (compound of the formula I in which $R_1$, $R_2$, $R_3$, $R_4$ and $R_5$=H) or a selectively protected compound of the formula II is reacted with activated acid derivatives of the formula (V)

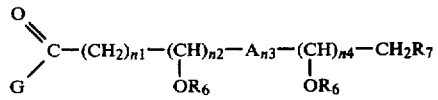

(V)

wherein $R_6$, $R_7$, A, $n_1$, $n_2$, $n_3$ and $n_4$ have the meaning already known and G represents an N-acylation reaction leaving group, preferably halogen or p-nitrophenoxy, or in which sisomicin or compounds of the formula (II) are reacted with compounds of the formula (V) wherein G denotes OH, in the presence of a catalyst or of a dehydrating agent, such as dicyclohexylcarbodiimide.

The acylation can be carried out by processes customary in peptide chemistry (see, for example, Houben-Weyl, Methoden der organischen Chemie (Methods of Organic Chemistry), Volume XV, Georg Thieme Verlag, Stuttgart, 1974).

In this case, $R_6$ advantageously denotes acyl or triarylmethyl, or 2 radicals $R_6$ together denote alkylidene, these substituents having the function of protective groups and preferably being split off again after the acylation.

A particularly preferred group of polyhydroxycarboxylic acids on which the compounds of the formula (V) are based are carboxyl derivatives of saccharides, such as gluconic acid.

The conversion of these carbohydrates into derivatives which are suitable for acylation reactions is known and is described, for example, in "Methods in Carbohydrate Chemistry", Academic Press—New York and London—Volume II, pages 11–35. Typical examples of such compounds are 2,3,4,5,6-penta-O-acetyl-D-gluconic acid chloride, 2,3,4,5-tetra-O-D-ribonic acid chloride, 2,3,4-tri-O-acetyl-D-ribonic acid chloride, 2,3,4,5,6-penta-O-benzoyl-D-gluconic acid chloride and 2,3,4,5-tetra-O-acetyl-L-arabonic acid.

The reactions of the selectively protected aminotrisaccharide derivatives of the formula II with the compounds of the formula (V) are preferably carried out in inert organic solvents, such as $CHCl_3$, DMF or pyridine, or mixtures of such solvents with alcohols, preferably methanol or ethanol.

Auxiliary bases which can be used are all the basic compounds customary in organic chemistry, such as, for example, triethylamine, pyridine or diazabicyclononene, or alkali metal hydroxides or carbonates, such as sodium hydroxide solution or sodium carbonate.

The acylation reactions are carried out at temperatures between −30° C. and +50° C., preferably between 0° C. and +25° C.

The reactions can be carried out either under normal pressure or under increased pressure. In general, they are carried out under normal pressure.

After the N-acylation, the N-protective and O-protective groups present in the molecule are split off in a manner which is in itself known.

The syntheses of the di-N-polyhydroxyacyl-aminotrisaccharides which the invention comprises can be carried out by partial N-acylations of the appropriately unprotected aminotrisaccharides, but in many cases it is more advantageous to introduce the appropriate polyhydroxyacyl groups stepwise by acylating the selectively blocked aminotri-saccharide of the formula (II) on the unblocked amino group by the processes described above, splitting off the protective groups again and then selectively introducing a further N-polyhydroxyacyl group.

The compounds according to the invention are antimicrobial agents with a broad spectrum of action and a particular activity against Gram-negative bacteria. These properties enable them to be used as medicaments, in particular for combating diseases, in warmblooded animals, caused by bacteria. They are very suitable, in medicine, for the prophylaxis and chemotherapy of local and systemic infections, in particular infections of the urogenital system, which are caused by Gram-negative bacteria, for example E. coli. Proteus, Klebsiella and Pseudomonas. In the agar hole test, inhibition areolas were found at a concentration of 100 micrograms/1 ml against, for example, the following strains of bacteria: Pseudomonas aerug. 5737, Pseudomonas aerug. F41, Klebsiella pneum. 2 Munich, Klebsiella pneum. 1 Dusseldorf, E. Coli Munster and E. coli Neumann, with the following compounds:

1-N[(S)-2,3-dihydroxypropyl)]-sisomicin,
1-N-[(S,R,S)-2,3,4,5-tetrahydroxypentyl]-sisomicin,
1-N-[(R,R,S)-2,3,4,5-tetrahydroxypentyl]-sisomicin and
1-N-[(S,R)-3,4,5-trihydroxypentyl]-sisomicin.

As stated above, the invention also relates to the use in medicine of the compounds of the invention.

The present invention provides pharmaceutical composition containing as active ingredient a compound of the invention in admixture with a solid or liquefied gaseous diluent, or in admixture with a liquid diluent other than a solvent of a molecular weight loss than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 20 to 2,000 mg, preferably 100 to 500 mg, of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably topically or parenterally, most preferably in liquid form as a solution or suspension for use on ears and eyes or for intramuscular injections. Preferred pharmaceutical compositions and medicaments are therefore those adapted for administration such as oral, topical or parenteral administration. Administration in the method of the invention is preferably oral, topical or parenteral administration.

In the case of parenteral administration it has proved advantageous to administer, in 2 to 4 doses per day, amounts of from 1 mg of 15 mg/kg of body weight to achieve effective results. The pharmaceutical compositions according to the invention when in the form of topical preparations generally contain from 0.1 to 3.0 g, of the active ingredient by weight per 100 g of ointment, cream or lotion. Topical administration is preferably effected 2 to 5 times daily. Nevertheless, it can at times be necessary to deviate from those dosage rates, and in particular to do so as a function of the nature and body weight of the warm-blooded animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The invention further relates to a medicated fodder comprising a compound of the present invention and a nutritious material. The addition of compounds of the present invention to the fodder promotes growth and improves feedstuff utilisation in animals.

Suitable formulations according to the present invention are illustrated in the following Tables.

Formulation 1

| | Tablet | 10 mg tablet | 25 mg tablet | 100 mg tablet |
|---|---|---|---|---|
| (a) | 1-N—[S—2,3-dihydroxypropyl]-sisomicin | 10.50+ mg | 26.25+ mg | 105.00+ mg |
| | lactose | 197.50 mg | 171.25 mg | 126.00 mg |
| | maize starch | 25.00 mg | 25.00 mg | 35.00 mg |
| | polyvinylpyrrolidone | 7.50 mg | 7.50 mg | 7.50 mg |
| | magnesium stearate | 2.50 mg | 2.50 mg | 3.50 mg |
| (b) | 1-N—[S,S,R—2,3,4,5-tetrahydroxypentyl]-sisomicin | 10.50+ mg | 26.25+ mg | 105.00+ mg |
| | lactose | 197.50 mg | 171.25 mg | 126.00 mg |
| | maize starch | 25.00 mg | 25.00 mg | 35.00 mg |
| | polyvinylpyrrolidone | 7.50 mg | 7.50 mg | 7.50 mg |
| | magnesium stearate | 2.50 mg | 2.50 mg | 3.50 mg |

+5% excess

To produce the tablets, a slurry of the active compound in question lactose and polyvinylpyrrolidone is prepared and this is spray-dried. The maize starch and magnesium stearate are added and the mixture is pressed to tablets.

Formulation 2

| Ointment | |
|---|---|
| 1-N—[S—2,3-dihydroxypropyl]-sisomicin | 1.0 g |
| methylparaben U.S.P. | 0.5 g |
| propylparaben U.S.P. | 0.1 g |
| petrolatum | to 1.000 g |

Preparation (1) The petrolatum is melted, (2) the active compound, methylparaben and propylparaben are mixed with about 10% of the molten petrolatum, (3) the mixture is introduced into a colloid mill and (4) the remainder of the petrolatum is added, whilst stirring, and the mixture is cooled until it becomes semi-solid. The product is filled into suitable containers.

Formulation 3

| Injection solution | Per 2.0 ml phial | Per 50 liters |
|---|---|---|
| 1-N—[S,S,R—2,3,4,5-tetra-hydroxypentyl]-sisomicin | 84.0 mg+ | 2,100.0 gm |
| methylparaben, U.S.P. | 3.6 mg | 90.0 gm |
| propylparaben, U.S.P. | 0.4 mg | 10.0 gm |
| sodium bisulphite, U.S.P. | 6.4 mg | 160.0 gm |
| disodium ethylenediamine-tetraacetate dihydrate | 0.2 mg | 5.0 mg |
| water, U.S.P. q.s. | 2.0 mg | 50.0 liters |

+5% excess

In the following examples which follow which illustrate the preparation of compounds according to the invention, the following running agent systems were used for determining the Rf value:

Running agent system A=methylene chloride:methanol:20% strength aqueous ammonia (2:4:1)

Running agent system B=methylene chloride:methanol:concentrated ammonia (2:2:1)

The thin layer chromatography was carried out on pre-coated silica gel plates from Messrs. Merck, Darmstadt.

EXAMPLE 1

1,2',3,6'-Tetra-N-acetyl-sisomicin 1.1 g of sisomicin are dissolved in 120 ml of water. After adding 60 ml methanol, 2.5 ml of acetic anhydride are added dropwise thereto, whilst stirring. After 15 minutes, the mixture is evaporated to dryness in vacuo. The residue is dissolved in 10 ml of methanol and this solution is added dropwise to a mixture of 30 ml of ether and 30 ml of petroleum ether, whereupon the desired product precipitates.

Yield=1.43 g, mass spectrum: m/e=615.

$^{13}$C-NMR ($CD_3OD$): $\delta$=50.14 (c-1); 49.20 (C-3); 46.88 (C-2'); 42.26 (C-6') and 173.24, 173.13 and 172.63 (>C=O) ppm.

EXAMPLE 2

1,3,3'',6'-Tetra-N-ethoxycarbonyl-sisomicin 450 mg of sisomicin are dissolved in 10 ml of water. After adding 10 ml of methanol, 870 mg of pyrocarbonic acid di-ethyl ester are added, whilst stirring well. After stirring the mixture at room temperature for 1.3 hours, 5 ml of water are added, the mixture is filtered and the filtrate is evaporated to dryness in vacuo. The residue is dissolved in methanol and the desired product is precipitated by adding ether and petroleum ether.

Yield=600 mg.

$^{13}$C-NMR ($CD_3OD$): $\delta$—66.01 (C-3''); 52.23 (C-1); 51.67 (C-3); 48.23 (C-2'); 43.74 (C-6'); and 157.69 (C=O) ppm.

EXAMPLE 3

2',3,3'',6'-Tetra-N-(o-nitrophenylsulphenyl)-sisomicin (3a) Penta-N-(o-nitrophenylsulphenyl)-sisomicin 38 g (0.10 mol) of o-nitrophenylsulphenyl chloride in 200 ml of dioxane, and 260 ml of 1 N NaOH are added to 13.84 g (20 mmols) of sisomicin sulphate in 100 ml of 1 N NaOH and 450 ml of freshly distilled dioxane so that the pH is between 12 and 14. The precipitate is filtered off and dissolved in $CH_2Cl_2/H_2O$ and the $CH_2Cl_2$ phase is dried with $Na_2SO_4$.

$CH_2Cl_2$ is added to the filtrate, the aqueous phase is discarded and the organic phase is dried over $Na_2SO_4$. The combined organic phases are evaporated to dryness and filtered over 250 g of silica gel (column diameter: 8 cm), first with $CH_2Cl_2$ and then with $CH_2Cl_2$/MeOH=97.5/2.5. The eluate gives, after evaporating off the solvent, 22 g (91%) of penta-N-(o-nitrophenylsulphenyl)-sisomicin as an orange-coloured foam.

13-C-NMR ($CDCl_3$): $\delta$=124—148 (aromatic H); 102.30 (O-1''); 99.00 (C-1'); 97.91 (C-4'); 89.05 (C-6'); 82.33 (C-4); 57.31 (C-1) and 56.73 (C-3) ppm.

(3b) 3''-N-(o-Nitrophenylsulphenyl)-sisomicin 160 ml of thiophenol are added to 16.0 g (13.2 mmols) of penta-N-NPS-sisomicin (NPS represents o-nitrophenylsulphenyl) in 80 ml of absolute pyridine and, after 1 hour, the mixture is poured onto 500 ml of diethyl ether, the precipitate is taken up in methylene chloride/methanol=8/2 and the solution is filtered over silica gel (column: 5.5×12 cm, running agent: methylene chloride/methanol=8/2, increasing addition of the running agent mixture methanol/methylene chloride/20 percent strength ammonia=4/2/1); the red zone gives, after evaporating off the solvent, 6.6 g (83%) of 3''-N-o-nitrophenylsulphenylsisomicin as a deep red foam.

13-C-NMR ($CD_3OD$): 33.59 ($CH_3N$); 52.23 (C-1); 51.16 (C-3); 53 (C-2') and 43.84 (C-6') ppm.

(3c)

2',3,3'',6'-Tetra-N-(o-nitrophenylsulphenyl)-sisomicin and 1,2',3'',6'-tetra-N-(o-nitrophenylsulphenyl)-sisomicin 4.4 g (15.0 mmols) of o-nitrophenylsulphenic acid p-nitrophenyl ester in 85 ml of methylene chloride are added to 3.0 g (5.0 mmols) of 3''-N-NPS-sisomicin in 5 ml of methanol and 45 ml of methylene chloride, the reaction mixture is immediately evaporated to dryness, the residue is taken up in methylene chloride and the methylene chloride solution is chromatographed on silica gel (column: 5.5×30 cm) with 200 ml of methylene chloride and then with methylene chloride/methanol. 500 fractions are collected, 1,2',3'',6'-tetra-NPS-sisomicin being obtained from combined fractions 150 to 250 and the 2',3,3'',6'-tetra-NPS derivative being obtained from fractions 270 to 500, both products being obtained as an orange-coloured foam.

1,2',3'',6'-Tetra-NPS-sisomicin: $R_F$ ($CH_2Cl_2/CH_3OH$=9/1): 0.62

IR(KBr): 1,501, 1,360 and 1,300 (intense); 1,587, 1,562 and 755 (medium); 1,442, 780 and 890 (weak) 2',3,3'',6'-

Tetra-NPS-sisomicin: $R_f(CH_2CH/CH_3OH=9/1)$: 0.42

IR (KBr): 1,500, 1,358 and 1,296 (intense); 1,586, 1,560 and 753 (medium); 1,442, 890 and 779 (weak)

EXAMPLE 4

3''-N-(2,3-Dihydroxypropyl)-sisomicin 400 mg of D,L-glyceraldehyde in 30 ml of methanol are added to 2.6 g of 1,2',3,6'-tetra-N-acetyl-sisomicin in 30 ml of water and the mixture is stirred at room temperature for 45 minutes. 360 mg of sodium cyanoborohydride are then added and the mixture is heated under reflux for 7.5 hours. For working up, it is stirred with a basic ion exchanger resin and filtered and the filtrate is evaporated to dryness in vacuo. The residue is digested with 30 ml of methylene chloride/methanol (4:1). The digestion mixture is filtered, the filtrate is evaporated in vacuo and 2.5 g of 3''-N-(2,3-dihydroxypropyl)-1,2',3,6'-tetra-N-acetylsisomicin are thus obtained as a colourless solid of melting point 130°-140° C. (decomposition).

To split off the acetyl groups, 1 g of the product described above is heated, in 10 ml of water, to the reflux temperature with 6 g of barium hydroxide octahydrate for 5 hours, the barium salts are removed by acidifying the mixture to pH 5.5 with 20% strength sulphuric acid and then centrifuging it and the centrifugate is evaporated to dryness in vacuo, after deionising with a basic ion exchanger resin. 510 mg of product of Rf value 0.37 (running agent system B+20% of (A) are obtained.

EXAMPLE 5

3''-N-[S,R,S-2,3,4,5-Tetrahydroxypentyl]-sisomicin

The procedure followed is as in Example 4, but L-arabinose is used as the aldehyde component. Rf value: 0.09 (running agent system A).

EXAMPLE 6

2'-N-[S,R,S-2,3,4,5-Tetrahydroxypentyl]-sisomicin 580 mg of 1,2,3'',6'-tetra-N-ethoxycarbonyl-sisomicin in 10 ml of water are stirred with 300 mg of L-arabinose and 10 ml of methanol at room temperature for 30 minutes. After adding 70 mg of sodium cyanoboranate, the mixture is heated to the reflux temperature for 5 hours and then worked up as described in Example 4. After splitting off the protective groups, 200 mg of the desired compound are obtained as an amorphous solid.

Rf value: 0.06 (running agent system A)

EXAMPLE 7

1-N-(2,3-Dihydroxypropyl)-sisomicin 1 g of 2',3,3'',6'-tetra-N-(o-nitrophenylsulphenyl)-sisomicin are dissolved in 10 ml of acetone and the solution is then heated to 70° C. with 300 mg of D,L-glyceraldehyde in 6 ml of acetone and 3.8 ml of water for 30 minutes. 250 mg of sodium cyanoboranate are then added and the mixture is heated for a further 2 hours. For working up, it is evaporated to dryness in vacuo, the residue is taken up in 20 ml of methylene chloride and the methylene chloride solution is washed twice with 10 ml of water each time. The organic phase is dried and evaporated and the residue thus obtained is chromatographed on a column charged with silica gel (eluting agent: methylene chloride/methanol 95:5). The fractions which contain the desired product in the pure form are combined and 600 mg of 1-N-(2,3-dihydroxypropyl)-2,3,3'',6'-tetra-N-(o-nitrophenylsulphenyl)-sisomicin are thus obtained; $[\alpha]_D^{22}=+78°$ (C=1.0 in $CH_2Cl_2$).

To split off the protective groups, the product is dissolved in 4 ml of methylene chloride, 8 ml of a saturated solution of hydrogen sulphide in methanol are added to this solution and the mixture is acidified with hydrochloric acid. The active compound is extracted with water, the aqueous phase is washed twice with methylene chloride and deionised with a basic ion exchanger and the solvent is evaporated off in vacuo. 250 mg of the desired compound are obtained as an amorphous solid; $[\alpha]_D^{22}=+113°$ (C=1.0 in $H_2O$).

1-N-[S-2,3-Dihydroxypropyl]-2,3,3'',6'-tetra-N-(o-nitrophenylsulphenyl)-sisomicin with $[\alpha]_D^{22}=+86°$ (C=1.0 in DMSO), and from this 1-N-[S-2,3-dihydroxypropyl]-sisomicin with $[\alpha]_D^{22}=+158°$ (C=1.0 in $CH_3OH$), is obtained in the same manner using D-glyceraldehyde.

EXAMPLE 8

1-N-[R,S,R-2,3,4,5-Tetrahydroxypentyl]-sisomicin 825 mg of 2',3,3'',6'-tetra-N-(o-nitrophenylsulphenyl)-sisomicin are dissolved in 16 ml of acetone and 3.75 ml of water. 800 ml of D-arabinose are added to this solution and the mixture is heated to 75° C. for 30 minutes. 250 mg of sodium cyanoborohydride are now added and the mixture is heated for a further 2 hours. It is worked up as described in Example 7 and the desired intermediate product is purified by column chromatography on silica gel using the eluting agent methylene chloride/methanol (9:1). 1-N-[R,S,R-2,3,4,5-Tetrahydroxypentyl]-2,3,3'',6'-tetra-N-(o-nitrophenylsulphenyl)-sisomicin is obtained as an orange-coloured solid. To split off the protective groups, a procedure analogous to Example 7 is followed and the desired compound is isolated by freeze-drying. $[\alpha]_D^{22}=+99°$ (C=1.0 in $H_2O$). In the same manner and using 3 2',3,3'',6'-tetra-N-(o-nitrophenylsulphenyl)-sisomicin and the particular hydroxyaldehydes indicated, the following compounds are obtained.

From D-ribose: 1-N-[R,R,S-2,3,4,5-tetrahydroxypentyl]-2',3,3'',6'-tetra-N-(o-nitrophenylsulphenyl)-sisomicin with $[\alpha]_D^{22}=+64°$ (C=1.0 in DMSO), and therefrom 1-N-[R,R,S-2,3,4,5-tetrahydroxypentyl]-sisomicin, Rf value=0.42 (running agent system B).

From L-arabinose: 1-N-[S,R,S-2,3,4,5-tetrahydroxypentyl]-2',3,3'',6'-tetra-N-(o-nitrophenysulphenyl)-sisomicin, $[\alpha]_D^{20}=+88°$ (C=1.0 in DMSO), and therefrom 1-N-[S,R,S-2,3,4,5-tetrahydroxypentyl]-sisomicin, $[\alpha]_D^{20}=+95°$ (C=1.0 in $H_2O$).

From L-rhamnose: 1-N-[S,S,S,S-2,3,4,5-tetrahydroxyhexyl]-2',3,3'',6'-tetra-N-(o-nitrophenysulphenyl)-sisomicin, $[\alpha]_D^{20}=+14°$ (C=1.0 in DMSO), and therefrom 1-N-[S,S,S,S-2,3,4,5-tetrahydroxyhexyl]-sisomicin, Rf value=0.57 (running agent system B).

From D-mannose: 1-N-[R,R,R,R-2,3,4,5,6-pentahydroxyhexyl]-2',3,3'',6'-tetra-N-(o-nitrophenylsulphenyl)-sisomicin, $[\alpha]_D^{22}=+47°$ (C=1.0 in DMSO), and therefrom 1-N-[R,R,R,R-2,3,4,5,6-pentahydroxyhexyl]-sisomicin, Rf value=0.34 (running agent system B).

From 2-desoxy-D-glucose: 1-N-[R,S,R-3,4,5,6-tetrahydroxyhexyl]-2',3,3'',6'-tetra-N-(o-nitrophenylsulphenyl)sisomicin, $[\alpha]_D^{22}=+82°$ (C=1.0 in DMSO), and therefrom 1-N-[R,S,R-3,4,5,6-tetrahydroxyhexyl]-sisomicin, $[\alpha_D^{22}=+33°$ (C=0.5 in $CH_3OH$).

From 2-Desoxy-D-ribose: 1-N-[S,R-3,4,5-trihydroxypentyl]2',3,3",6'-tetra-N-(o-nitrophenylsulphenyl)-sisomicin, $[\alpha]_D^{22}=+74°$ (C=1.0 in DMSO), and therefrom 1-N-[S,R-3,4,5-trihydroxypentyl]-sisomicin, $[\alpha]_D^{22}=+21°$ (C=1.0 in $CH_3OH$).

From 2-desoxy-D-galactose: 1-N-[R,R,R-3,4,5,6-tetrahydroxyhexyl]-2',3,3",6'-tetra-N-(o-nitrophenylsulphenyl)sisomicin, $[\alpha]_D^{22}=+73°$ (C=1.0 in DMSO), and therefrom 1-N-[R,R,R-3,4,5,6-tetrahydroxyhexyl]-sisomicin, Rf value=0.07 (running agent system A).

From D-xylose: 1-N-[S,R,R-2,3,4,5-tetrahydroxypentyl]2',3,3",6'-tetra-N-(o-nitrophenylsulphenyl)-sisomicin, $[\alpha]_D^{22}=+49°$ (C=1.0 in DMSO), and therefrom 1-N-[S,R,R-2,3,4,5-tetrahydroxypentyl]-sisomicin, Rf value=0.3 (running agent system B).

EXAMPLE 9

1-N-[S-2,3-Isopropylideneoxypropyl]-sisomicin 600 mg of 2',3,3",6'-tetra-N-(o-nitrophenylsulphenyl)-sisomicin are heated to 50° C., in 10 ml of acetone and 2.2 ml of water, with 400 mg of 2,3-O-isopropylidene-D-glyceraldehyde for 30 minutes.

150 mg of sodium cyanoborohydride are then added and the mixture is heated for a further 3 hours. It is then worked up analogously to Example 4 and the 1-N-[S-2,3-isopropylideneoxypropyl]-2',3,3",6'-tetra-N-(o-nitrophenylsulphenyl)-sisomicin is isolated by column chromatography on silica gel using methylene chloride/methanol (9.5:0.5) as the eluting agent; $[\alpha]_D^{22}=+62°$ (C=1.0 in DMSO). The splitting off is carried out analogously to Example 5 and gives the desired compound as an amorphous solid; $[\alpha]_D^{22}=+92°$ (c=1.0 in $CH_3OH$).

EXAMPLE 10

1-N-[R,S,R,R-2,3,4,5,6-Pentahydroxyhexanoyl]-sisomicin 425 mg of penta-O-acetyl-D-gluconic acid chloride in 1 ml of absolute methylene chloride are added, in 3 portions, to 220 mg of 2',3,3",6'-tetra-N-(o-nitrophenylsulphenyl)-sisomicin in 2 ml of absolute methylene chloride and 0.2 ml of absolute pyridine in the course of 2 hours. The reaction mixture is left to stand at room temperature for 3 hours and then stirred overnight with 1 ml of concentrated ammonia and 1 ml of methanol. The reaction mixture is evaporated to dryness and, in order to split off the protective groups, is treated in a manner analogous to Example 4. 80 mg of a colourless powder are obtained, Rf value=0.07 (running agent system A).

EXAMPLE 11

3-N-[R,S,R,R-2,3,4,5,6-Pentahydroxyhexanoyl]-sisomicin

The preparation is analogous to Example 10, starting from 220 mg of 1,2',3",6'-tetra-N-(o-nitrophenylsulphenyl)-sisomicin. The yield is 70 mg, Rf value=0.17 (running agent system B).

EXAMPLE 12

1-N-(2,2-bis-hydroxymethylpropionyl)-sisomicin

The preparation is analogous to Example 10, starting from 220 mg of 2',3,3",6'-tetra-N-(o-nitrophenylsulphenyl)-sisomicin and 70 μl of 2,2-bis-acetoxymethylpropionyl chloride. 60 mg of the desired compound are obtained with a Rf value=0.7 (running agent system B).

EXAMPLE 13

1-N-(2,3-Dihydroxypropionyl)-sisomicin

13 (a) 2,3-O-Cyclohexylideneglyceric acid 4-nitrophenyl ester 1.2 g of the potassium salt of 2,3-O-cyclohexylideneglyceric acid are dissolved in 10 ml of water, the solution is acidified to pH 3.8 with 1 N hydrochloric acid at −10° C. and extracted immediately with methylene chloride and the extract is dried with sodium sulphate. 0.4 ml of pyridine and 0.7 g of 4-nitrophenol are added at 0° C., and a solution of 1.03 g of dicyclohexylcarbodiimide in 5 ml of methylene chloride is added dropwise. After 15 hours, dicyclohexylurea is filtered off, the filtrate is washed with 5% strength aqueous sodium bicarbonate solution and water, dried with sodium sulphate and concentrated and the solid residue is stirred with a little isopropanol and dried. 0.6 g of product is obtained with a characteristic IR band at 1,780 $cm^{-1}$.

13 (b) Acylation 165 mg of 2',3,3",6'-tetra-N-(o-nitrophenylsulphenyl)-sisomicin are dissolved in 0.75 ml of pyridine and the solution is stirred with 57 mg of 2,3-O-cyclohexylideneglyceric acid 4-nitrophenyl ester at room temperature for 24 hours and evaporated to dryness. The reaction product is freed from a small amount of impurities by chromatography on a little silica gel using methylene chloride/methanol (95:5) as the eluting agent. The protective groups are removed analogously to Example 7, whereupon the acid solution obtained after the splitting is left to stand at room temperature for about 30 minutes in order to quantitatively split off the cyclohexylidene radicals. 35 mg of product are obtained with a Rf value=0.20 (running agent system A).

EXAMPLE 14

1-N-(2,3-Dihydroxypropyl)-sisomicin

1-N-(2,3-Dihydroxypropionyl)-sisomicin is reduced with lithium aluminum hydride in absolute tetrahydrofurane and 1-N-(2,3-dihydroxypropyl)-sisomicin, which is identical to the product from Example 7, is obtained.

EXAMPLE 15

1-N-[S,R,R,R-2,3,4,5,6-Pentahydroxyhexyl]-sisomicin

1-N-[R,S,R,R-2,3,4,5,6-Pentahydroxyhexanoyl]-sisomicin is reduced with lithium aluminium hydride in absolute tetrahydrofurane and the title compound is obtained with a Rf value—0.29 (running agent system B).

Among the new pseudotrisaccharide salts of the invention, those salts that are pharmaceutically acceptable are particularly important and are preferred.

The new free pesudotrisaccharides of the general formula I and their salts can be interconverted in any suitable manner; methods for such interconversion are known in the art.

The present invention also comprises pharmaceutically acceptable bioprecursors of the active compounds of the present invention.

For the purposes of this specification the term pharmaceutically acceptable bioprecursor of an active compound of the invention means a compound having a structural formula different from the active compound but which nonetheless, upon administration to an animal or human being is converted in the patient's body to the active compound.

What is claimed is:

[1. A pseudotrisaccharide of the formula

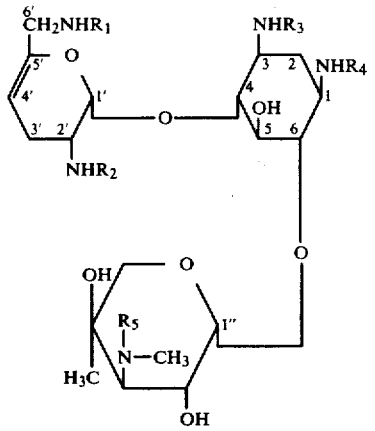

(1)

or a salt thereof in which $R_1$, $R_2$, $R_3$, $R_4$ and $R_5$ independently of one another denote hydrogen or a group of the formula $$CH_2-(CH_2)_{n1}-\underset{\underset{OR_6}{|}}{(CH)}_{n2}-A_{n3}-\underset{\underset{OR_6}{|}}{(CH)}_{n4}-CH_2R_7 \quad \text{(Ia)}$$

in which

A denotes $$-CH=CH- \text{ or } [-CH_{(2-n5)}-(CH_2OR_6)_{n5}]$$

$R_6$ denotes hydrogen; triphenylmethyl; triphenylmethyl substituted by $C_1$-$C_4$-alkyl or chloro; $C_1$-$C_4$-alkyl; $C_2$-$C_6$-alkylcarbonyl; formyl or benzoyl; or 2 $R_6$ together denote $C_1$-$C_6$-alkylidene, $R_7$ denotes hydrogen or $OR_6$, $n_1$ is 0, 1, 2 or 3, $n_2$ is 0, 1, 2, 3, 4 or 5 and $n_3$, $n_4$ and $n_5$ are, independently of one another, 0, 1 or 2, the sum of $n_1$, $n_2$, $n_3$ and $n_4$ being from 1 to 5 and the total number of the $OR_6$ groups in at least one of $R_1$, $R_2$, $R_3$, $R_4$ and $R_5$ being 2 to 6, and at least one of the $R_1$, $R_2$, $R_3$, $R_4$ and $R_5$ being other than hydrogen.]

[2. A compound according to claim 1, in which $R_4$ and one of $R_1$ and $R_2$ denotes the group of the formula (Ia) as defined in claim 1, and $R_3$ and $R_5$ and the other one of $R_1$ and $R_2$ denote hydrogen.]

[3. A compound according to claim 1, in which $R_1$, $R_2$, $R_3$ and $R_5$ denote hydrogen and $R_4$ denotes the group of the formula (Ia) as defined in claim 1.]

[4. A compound according to any of the foregoing claims, in which $n_3$ and $n_4$ are 0 and the sum of $n_1$ and $n_2$ is 1, 2 or 3.]

5. An antibacterial pharmaceutical composition containing as an active ingredient an antibacterially effective amount of a compound according to claim [1] *13* in admixture with an inert pharmaceutical carrier.

6. An antibacterial pharmaceutical composition of claim 5 in the form of a sterile or physiologically isotonic aqueous solution.

7. A composition according to claim 5 when in the form of a topical preparation containing from 0.1 to 3.0 g of the said active ingredient, per 100 g of ointment, cream or lotion.

8. A medicament according to claim 5 in the form of tablets, pills, dragees, capsules, ampoules, or suppositories.

9. A method of combating bacterial diseases in warm-blooded animals which comprises administering to the animals an antibacterially effective amount of active compound according to claim [1] *13* either alone or in admixture with an inert pharmaceutical carrier.

10. A method according to claim 9 in which the active compound is administered parenterally in an amount of 1 to 15 mg per kg body weight per day.

11. A method according to claim 9 in which the active compound is administered orally, topically or parenterally.

12. A medicated fodder comprising an active compound according to claim [1] *13* and a nutritious carrier material.

*13. A compound according to the formula*

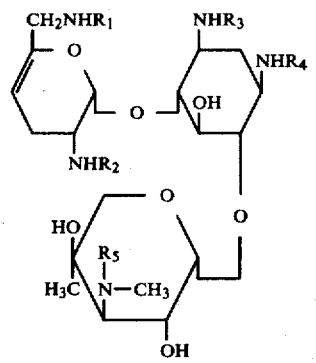

*wherein*

*$R_1$, $R_2$, $R_3$, $R_4$ and $R_5$ independently represent a radical selected from the group consisting of hydrogen, 2,3,4-trihydroxypentyl-,3,4,5-trihydroxypentyl-,2,3,4,5-tetrahydroxypentyl-,2,4,5-trihydroxyhexyl-, 4,5,6-trihydroxyhexyl-, 2,3,4,5-tetrahydroxyhexyl-,3,4,5,6-tetrahydroxyhexyl-, 2,4,5,6-tetrahydroxyhexyl-, 4,5-dihydroxy-pent-2-en-1-yl-, 4,5-dihydroxy-hex-2-en-1-yl and 4,5,6-trihydroxy-hex-2-en-1-yl-, with the proviso that at least one of the radicals $R_1$ to $R_5$ being other than hydrogen.*

* * * * *

UNITED STATES PATENT AND TRADEMARK OFFICE

CERTIFICATE OF CORRECTION

PATENT NO. : Re. 31,512

DATED : January 31, 1984

INVENTOR(S) : Peter Stadler et al

It is certified that error appears in the above-identified patent and that said Letters Patent is hereby corrected as shown below:

| | |
|---|---|
| Col. 3, line 37 | Beginning of line delete "[S,S(S-" and insert --[S,S,S- -- |
| Col. 14, line 60 | Insert omitted claim in italics |

--14. 1-N-(2,3,4,5-tetrahydroxypentyl)-sisomicin. --

Signed and Sealed this

Tenth Day of July 1984

[SEAL]

*Attest:*

GERALD J. MOSSINGHOFF

*Attesting Officer*

*Commissioner of Patents and Trademarks*